United States Patent [19]
Helland et al.

[11] Patent Number: 5,545,201
[45] Date of Patent: Aug. 13, 1996

[54] BIPOLAR ACTIVE FIXATION LEAD FOR SENSING AND PACING THE HEART

[75] Inventors: John R. Helland, Redmond, Wash.; Hong Li, Arcadia, Calif.

[73] Assignee: Pacesetter, Inc., Sylmar, Calif.

[21] Appl. No.: 412,649

[22] Filed: Mar. 29, 1995

[51] Int. Cl.⁶ .................................................. A61N 1/05
[52] U.S. Cl. .............................. 607/127; 128/642
[58] Field of Search .................... 607/127, 37, 118, 607/122, 125, 126, 131, 132; 128/642

[56] References Cited

U.S. PATENT DOCUMENTS

| | | | |
|---|---|---|---|
| 4,010,758 | 3/1977 | Rockland et al. | 128/418 |
| 4,355,642 | 10/1982 | Alferness | 128/642 |
| 4,541,440 | 9/1985 | Parsonnet | 607/132 |
| 4,628,943 | 12/1986 | Miller | 128/785 |
| 4,972,848 | 11/1990 | Di Domenico et al. | 128/785 |
| 5,020,545 | 6/1991 | Soukup | 128/785 |
| 5,217,028 | 6/1993 | Dutcher et al. | 128/785 |
| 5,324,323 | 6/1994 | Bui | 607/132 |
| 5,342,414 | 8/1994 | Mehra | 607/127 |

FOREIGN PATENT DOCUMENTS 2120787  7/1972  France ................... 128/642

Primary Examiner—William E. Kamm
Assistant Examiner—George R. Evanisko
Attorney, Agent, or Firm—Harold C. Schloss

[57] ABSTRACT

An implantable bipolar pacing lead having a bipolar active fixation electrode for use with a cardiac pacemaker. The bipolar active fixation electrode may include a pair of coaxial electrodes, separated by an intermediate insulator, formed into the shape of a helix. The bipolar electrode helix is preferably advanceable from a distal end of the bipolar pacing lead.

27 Claims, 2 Drawing Sheets

BIPOLAR ACTIVE FIXATION LEAD FOR SENSING AND PACING THE HEART

FIELD OF THE INVENTION

This invention relates generally to an implantable stimulation lead for use with an implantable pulse generator such as a cardiac pacemaker. More specifically, the invention relates to an implantable stimulation lead having a bipolar active fixation electrode for pacing and sensing electrical activity in the heart.

BACKGROUND OF THE INVENTION

Pacing leads having at least two electrodes at the distal end are in use for bipolar pacing, as well as for providing sensory information to an attached cardiac pacemaker. Generally, bipolar pacing leads are either active or passive fixation, the former using tines typically, and the latter using a screw mechanism. A bipolar active fixation lead can have its helical screw be one of its electrodes and a ring electrode spaced from the distal end of the pacing lead as its second electrode. The spacing between the two electrodes is usually dependent upon the physical constraints attendant with the design of the distal end of the lead and its materials. However, it is beneficial to have the two electrodes very close together, particularly for sensing differences in the electrical signals in the heart.

The design and proximity of the electrodes can be such as to enhance the electrical signal sensing capability of the bipolar lead to allow improved discrimination of the sensed signals. Generally, abnormal electrical activity such as ventricular tachycardia or ventricular fibrillation results in electrical signals having differing characteristics. For example, in a given patient, ventricular tachycardia may produce electrical potentials much higher than normal sinus rhythm. By comparison, ventricular fibrillation may produce electrical potentials which are smaller than that of normal sinus rhythm signals. The ability of a pacing lead to discriminate between the signals is at least partially dependent upon the spacing between the two electrodes. The ability to sense the electrical potential across a small area within the myocardial tissue would be very beneficial in allowing a pacing system to discriminate between the various electrical signals within the heart. In addition, minimizing the spacing between the electrodes used for bipolar sensing would also minimize the sensing of "far field" electrical signals generated within the chest cavity.

In view of the above characteristics of a pacing system, a bipolar lead having a very small separation between the respective anode and cathode electrodes is desirable to enhance the sensing capability of the bipolar lead. This enhanced sensing capability would improve the ability of the implantable pulse generator to discriminate ventricular tachycardia from ventricular fibrillation from normal sinus rhythm. If the lead is used in conjunction with an implantable defibrillator, the ability to discriminate between these conditions can be used to determine the kind of therapy to be provided.

SUMMARY OF THE INVENTION

The present invention is directed to an implantable bipolar pacing lead having a bipolar active fixation electrode for use with a cardiac pacemaker or an implantable defibrillator. The bipolar active fixation electrode may include a pair of coaxial electrodes, separated by an insulator, formed into the shape of a helix. The bipolar electrode helix is preferably advanceable from a distal end of the bipolar pacing lead. At the tip of the bipolar electrode helix, the outer electrode is removed, so that the intermediate insulator and the inner electrode extend from the outer electrode, spacing the two electrodes a distance of between 0.1 and 5.0 mm.

DETAILED DESCRIPTION OF THE PREFERRED EMBODIMENT

Figure 1:
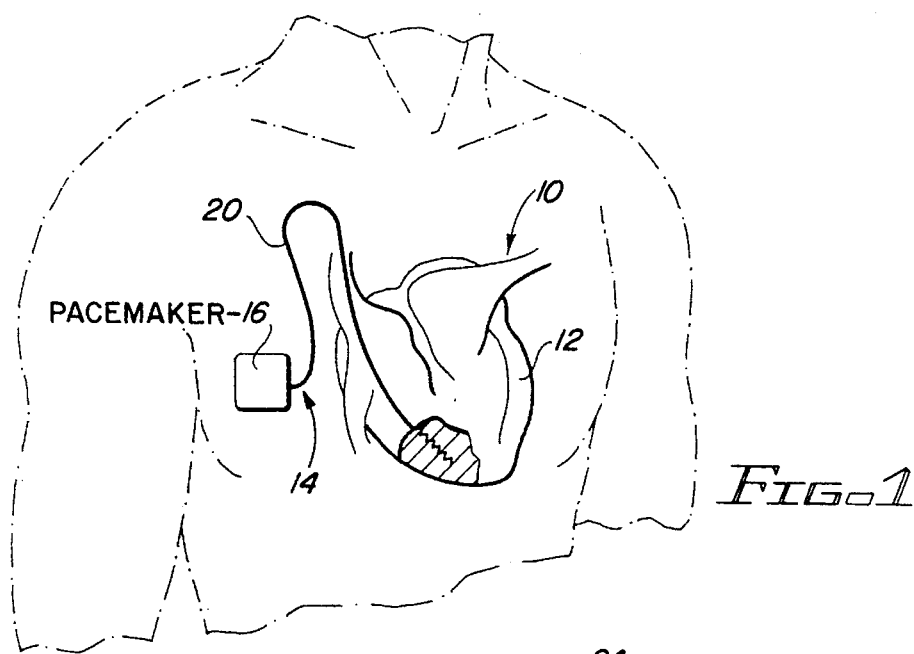
FIG. 1 depicts an implanted pacing system including a bipolar pacing lead according to the present invention.

FIG. 1 depicts a chest cavity 10 in phantom, and the heart 12 therein. A pacing system 14 including a pacemaker 16 and a bipolar pacing lead 20 according to the present invention are depicted as being implanted in the chest cavity 10.

Figure 2:
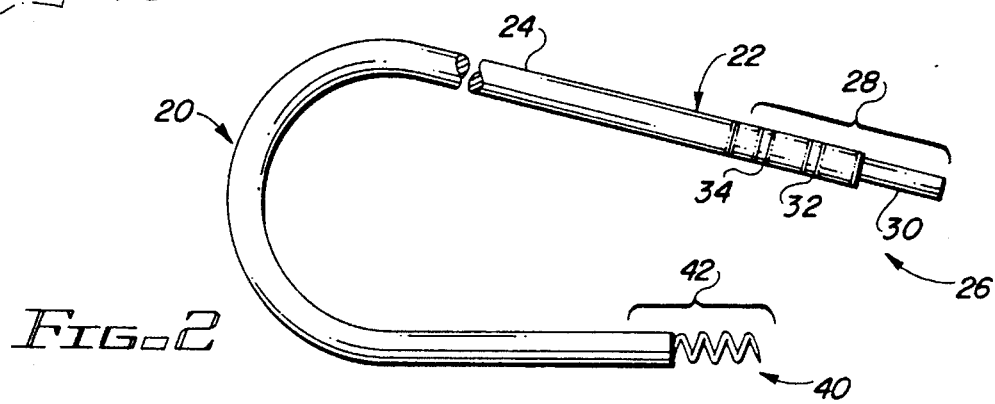
FIG. 2 depicts the bipolar pacing lead of FIG. 1.

The bipolar pacing lead 20 is depicted in FIG. 2. The bipolar pacing lead 20 includes an elongated lead body 22 which includes at least two electrical conductors (described below) within an insulation sheath 24. The insulation sheath 24 is preferably fabricated from a flexible biocompatible material such as silicone rubber, polyurethane or other suitable plastic.

The bipolar pacing lead 20 has a proximal end 26 including a connector assembly 28, which is configured to be inserted into a receiving orifice in the pacemaker 16 (FIG. 1). The connector assembly 28 includes at least two electrical terminals 30, 32 (and 34) each being connected to a respective one of the at least two electrical conductors extending through the lead body 22. The bipolar pacing lead 20 is preferably constructed to include a hollow interior extending from the proximal end 26 of the bipolar pacing lead 20 to its distal end 40. The hollow interior allows the introduction of a stylet (not shown) during implant, which is beneficial in allowing guiding of the otherwise flexible bipolar pacing lead 20 from the point of venous insertion to the implant situs. The bipolar pacing lead 20 also includes an electrode assembly 42 at the distal end 40.

Figure 3:
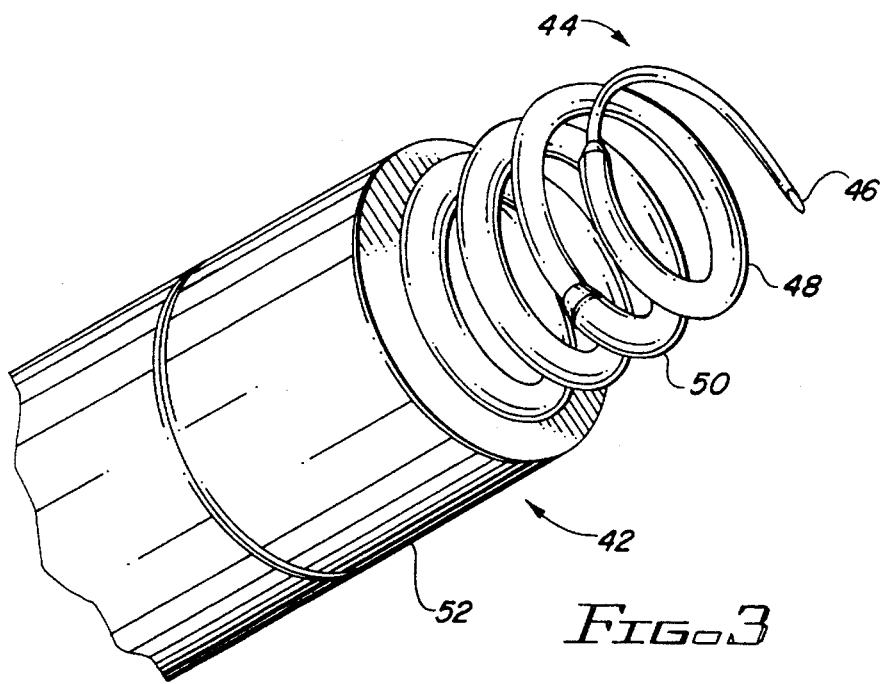
FIG. 3 shows a perspective view of the distal tip of the bipolar pacing lead of FIG. 2.

The electrode assembly 42, depicted in the enlarged perspective view of FIG. 3, is a bipolar active fixation electrode having a helix 44 defining a center electrode 46, an intermediate insulator 48, and an outer electrode 50. The helix 44 may be either fixed or advanceable from a cylindrical sheath 52 at the distal end of the lead body 22. The cylindrical sheath 52 may be formed as a rigid insulator, or alternately, the cylindrical sheath 52 may include conductive electrode material, which may be electrically connected to the outer electrode 50 of helix 44, as discussed below. The electrode assembly 42 depicted in FIG. 3 is configured so that the helix 44 is advanceable to penetrate the myocardium of the heart 12 (FIG. 1) upon implantation.

Figure 4:
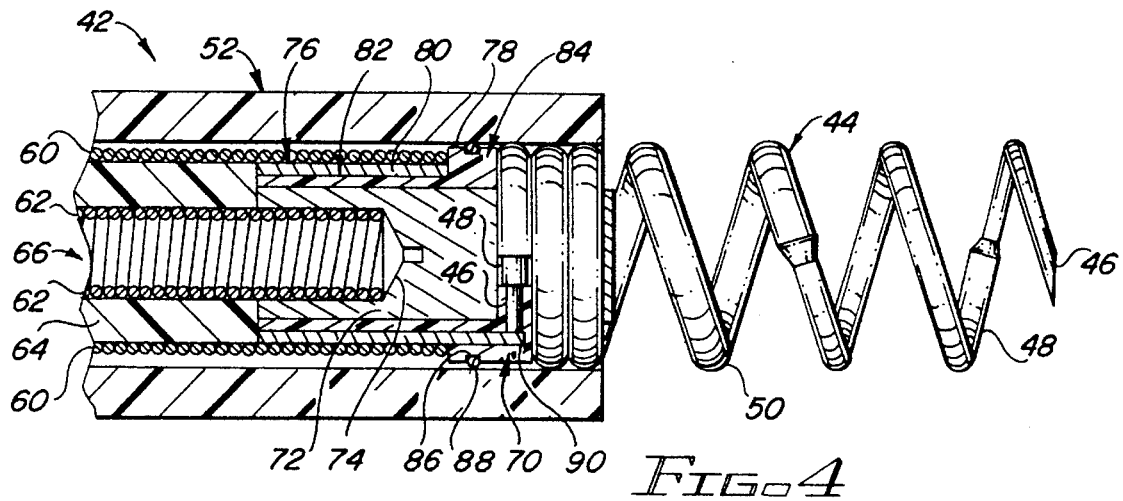
FIG. 4 shows an enlarged partial cross-sectional view of a portion of the distal tip of the bipolar pacing lead of FIG. 2.

A detailed partial cross sectional view of the electrode assembly 42 is depicted in FIG. 4. As depicted in FIG. 4, the lead body 22 includes a first conductor 60 and a second conductor 62 within the insulation sheath 24. The first and second conductors 60 and 62 are preferably coaxial helical conductors separated by an insulator 64. As depicted, the internal surface of the second conductor 62 defines an internal axial passageway 66, allowing insertion of a stylet (not shown) through the lead body 22. However, the first and second conductors 60 and 62 do not have to be coaxial conductors. For example, it is within the spirit of the invention that the conductors 60 and 62 could be side-by-side or parallel conductors. Additionally, conductor 60 does not have to be a wire, nor does 62 have to be a tubular conductor. Either conductor 60 or 62 could be a wire, a coiled conductor, tubular, coaxial, parallel, etc., providing that they act together as a bipolar electrode.

The electrode assembly 42 receives the first conductor 60 and second conductor 62 extending through the lead body 22, which are to be electrically connected to the center electrode 46 and the outer electrode 50 of helix 44, respectively. In order to prevent fluids from invading the lead body 22, the electrode assembly 42 includes an interconnect plug 70. The interconnect plug 70 provides the electrical interconnections between the first and second conductors 60 and 62 and the center and outer electrodes 46 and 50 respectively, while also blocking fluid invasion into the lead body 22. The interconnect plug 70 may be fixed with respect to the cylindrical sheath 52, or movable if required to advance the helix 44 axially with respect to the distal end of the cylindrical sheath 52.

The interconnect plug 70 is preferably an assembly including a central conductive cylinder 72 having an internal bore 74, at its end which extends toward the lead body 22, to receive the second conductor 62. The opposite end of the central conductive cylinder 72 projects outward and forms a cylinder about which a proximal end of the helix 44, and specifically the outer electrode 50 thereof, can be affixed.

The interconnect plug 70 may also include a sleeve 76 secured about the central conductive cylinder 72. The sleeve 76 may include a stepped cylindrical insulator 78 and a conductive cylinder 80 formed about an outer portion 82 of the stepped cylindrical insulator 78. The conductive cylinder 80 is configured to be inserted internally into the first conductor 60 of the lead body and electrically secured thereto. The stepped cylindrical insulator 78 includes a ridge 84 extending radially outward to an outer diameter which closely matches the internal diameter of the cylindrical sheath 52. The ridge 84 may include a recess 86 which receives an o-ring 88 to seal against the internal diameter of the cylindrical sheath 52.

The interconnect plug 70 also includes a conductor 90 extending through the ridge 84. The conductor 90 is electrically connected (for example, either by welding or soldering) to the center electrode 46 of helix 44.

Figure 5:
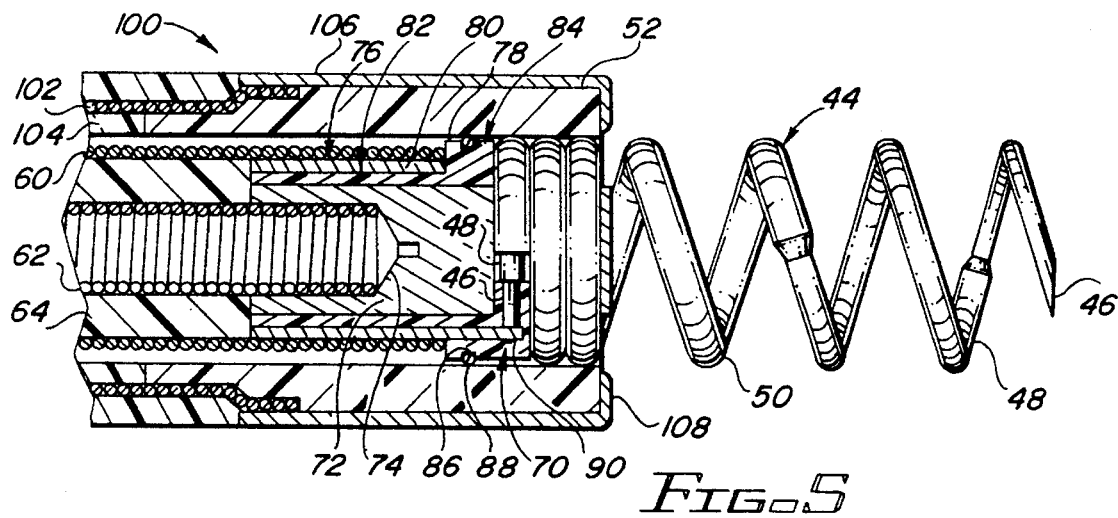
FIG. 5 shows an enlarged partial cross-sectional view of an alternative embodiment for the assembly at the distal tip of the bipolar pacing lead of FIG. 2.

FIG. 5 depicts a partial cross sectional view of the distal end 100 of a first alternative embodiment for a bipolar pacing lead, which is substantially similar to the bipolar pacing lead 20 of FIGS. 1–4, and like elements are designated by like numbers and the foregoing description is incorporated. Thus, in the embodiment of FIG. 5, only the modifications from the detailed description of FIG. 4 will be discussed.

In FIG. 5, the lead body 22 includes a third conductor 102 which may be a helical conductor positioned coaxially with respect to the first conductor 60 and spaced therefrom by an insulator 104. The third conductor flares out at its distal end about the cylindrical sheath 52, into electrical contact with a sleeve electrode 106 affixed to the outer surface of cylindrical sheath 52. The sleeve electrode 106 may include a radially inwardly extending lip 108 at its most distal end. The sleeve electrode 106 may be utilized as a redundant anode electrode in a bipolar pacing system with the center electrode 46 of the helix 44 acting as the cathode.

Alternatively, the second conductor 62 and the third conductor 102 may be connected at their proximal ends so that both the outer electrode 50 on helix 44 and the sleeve electrode 106 act as cathode electrodes. The advantage of connecting the sleeve electrode 106 to the outer electrode 50 is the potential of larger signal strength due to the larger electrode area.

As another alternative, the third conductor 102 may be interconnected at its proximal end to a third electrical terminal 34 (FIG. 2) located on the connector assembly 28. This configuration would allow the sleeve electrode 106 to serve as a backup electrode in the event of a failure in either of the electrodes 46 or 50 positioned on the helix 44, or a failure in one of their respective conductors 60 and 62.

In the preferred embodiments, the diameter of the helix 44 is preferably about 2.0 millimeters. The center electrode 46 is formed from a wire having a diameter of between about 0.004 inches and 0.008 inches. The intermediate insulator 48 has a wall thickness of between about 0.001 and 0.0025 inches and may be formed from a suitable polymer such as polyurethane or polytetrafluoroethylene (PTFE), silicone rubber, or Tefzel material. The outer electrode 50 preferably has an outer diameter of between about 0.009 inches and 0.0015 inches. The exposed surface area of the center electrode 46 extends back from its tip a distance of between about 1 and 2 millimeters. The outer electrode 50 is preferably spaced from the exposed portion of the central electrode 46 a distance of between about 0.1 and 5 millimeters. Accordingly, the separation distance between the respective elements defining the bipolar electrode is on the order of between about 0.1 and 5 millimeters. Preferably, the separation distance is between 0.5 and 1.5 millimeters.

The outer electrode 50 may be formed upon the intermediate insulator 48 by a process such as vapor deposition or electroplating. Alternatively, the central electrode 46 may be formed from a straight conductor which is coated with a suitable insulator such as polyurethane, polytetrafluoroethylene (PTFE), silicone rubber, or Tefzel to form the intermediate insulator 48, and then the two elements are inserted into a hollow sleeve defining the outer electrode 50. Subsequently, the coaxial conductor and intermediate insulator can be formed into the helix 44.

In another embodiment the central electrode 46, the outer electrode 50 and the sleeve electrode 106 may include a porous or microporous coating to improve sensing capabilities.

Figure 6:
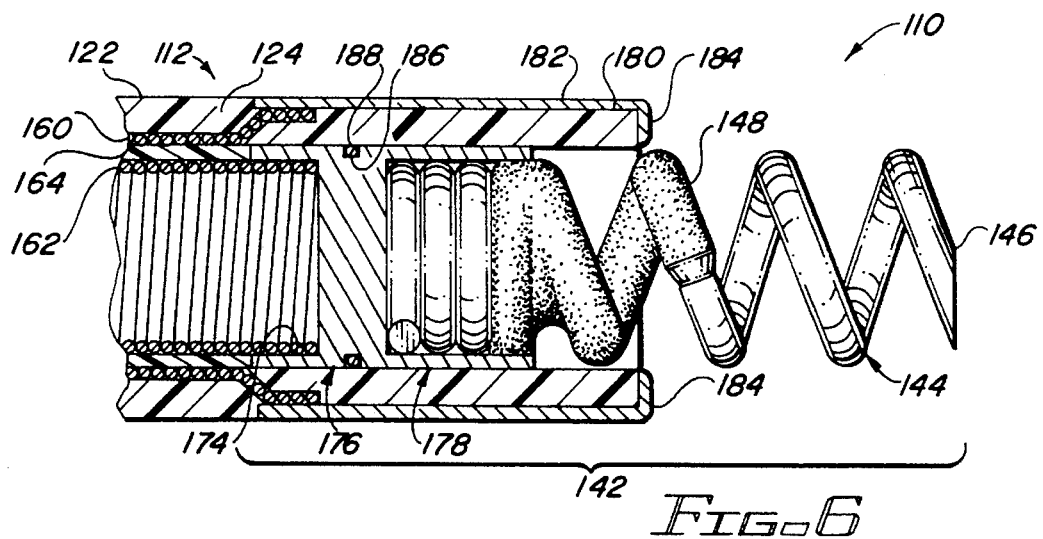
FIG. 6 shows an enlarged partial cross-sectional view of another alternative embodiment for assembly at the distal tip of the bipolar pacing lead of FIG. 2.

Another alternative embodiment is depicted in the partial cross sectional view of the distal end 110 of a bipolar pacing lead 112 shown in FIG. 6. In the embodiment of FIG. 6, a bipolar electrode assembly 142 includes an active fixation helix electrode 144, and an electrode sleeve 182. The bipolar electrode assembly 142 is secured to the distal end 110 of a lead body 122, which is otherwise essentially identical to the lead body 22 detailed above with respect to FIGS. 1–4.

The lead body 122 includes a first conductor 160 and a second conductor 162, within an insulation sheath 124. The conductors 160 and 162 may be separated by an insulator 164. At the distal end of the lead body 122, the first conductor 160 is flared outward about a rigid insulating element 180, and into electrical contact with the electrode sleeve 182 formed about or secured to the rigid insulating element 180. The electrode sleeve 182 may include a radially inwardly extending lip 184 at its most distal end. The electrode sleeve 182 acts as the anode in a bipolar pacing configuration, with the active fixation helix electrode 146 serving as the cathode, or vice versa.

In the embodiment of FIG. 6, the active fixation helix electrode 144 is formed from an electrode wire 146 and is secured to a conductive plug 176. The conductive plug 176 may be movable or fixed with respect to the lead body 122 and rigid insulating element 180. The active fixation helix electrode 144 may include an insulator 148 coating at least a portion of the electrode wire 146, as well as the exposed portions of the conductive plug 176. The conductive plug 176 includes an axial bore 174 on its end which extends toward the lead body 122, which receives and is electrically interconnected to the second conductor 162.

The conductive plug 176 also includes a wall 178 to prevent fluid invasion axially into the lead body 122. The outer diameter of the conductive plug 176 is sized to closely match the inner diameter of the rigid insulating element 180 to prevent fluid invasion. However, the conductive plug 176 preferably includes a recess 186 receiving an o-ring 188 to seal against an internal diameter of the rigid insulating element 180.

By the configuration according to FIG. 6, the bipolar electrodes remain closely spaced, although only one electrode is included on the active fixation helix. By coating a portion of the electrode wire 146 of the active fixation helix electrode 144 with the insulator 148, the separation between the respective electrodes becomes variable during implantation based upon how far the active fixation helix is advanced with respect to the rigid insulating element 180, and electrode sleeve 182 thereof. It should also be apparent that the inwardly extending lip 184 of the electrode sleeve 182 will be in intimate contact with the myocardial tissue, and the shortest electrical path between the two electrodes will be through the muscle tissue of the myocardium.

It should be evident from the foregoing description that the present invention provides many advantages over pacing leads of the prior art. Although preferred embodiments are specifically illustrated herein, it will be appreciated to those skilled in the art that many modifications and variations of the present invention are possible. It is therefore preferred that the present invention be limited only by the proper scope of the appended claims.

What is claimed is:

1. An implantable lead for use with an implantable medical device, comprising:

a lead body having a proximal end and a distal end, said lead body including at least two electrical conductors extending from said proximal end to said distal end of said lead body;

an electrical connector coupled to said proximal end of said lead body and including at least two terminals electrically connected to respective ones of said at least two conductors; and an electrode assembly comprising an active fixation helix coupled to said distal end of said lead body, said active fixation helix comprising:

a pair of electrodes separated by an intermediate insulator; and means for electrically interconnecting each of said pair of electrodes to a respective one of said at least two electrical conductors of said lead body.

2. The implantable lead of claim 1, wherein said pair of electrodes comprises:

a center electrode; and an outer electrode, said center electrode and said outer electrode being electrically separated by said intermediate insulator.

3. The implantable lead of claim 2, wherein said electrode assembly further comprises:

an interconnect plug for providing an electrical interconnection between said at least two conductors of said lead body and said center electrode and said outer electrode.

4. The implantable lead of claim 3, wherein said interconnect plug includes means for blocking fluid invasion into said lead body.

5. The implantable lead of claim 1, wherein:

said lead body includes a cylindrical sheath attached to said distal end of said lead body, wherein said pair of electrodes are movable relative to said cylindrical sheath.

6. The implantable lead of claim 5, further comprising:

a sleeve electrode affixed to an outer surface of said cylindrical sheath; and a third electrical conductor within said lead body and extending from said proximal end of said lead body to said distal end of said lead body, said third conductor having a distal end interconnected to said sleeve electrode.

7. The implantable lead of claim 6, wherein said electrical connector further includes a third terminal coupled to said third electrical conductor; and whereby said sleeve electrode is electrically connected to said third terminal and acts as an alternate electrode.

8. The implantable lead of claim 6, wherein one of said pair of electrodes and the sleeve electrode are electrically connected together.

9. The implantable lead of claim 1, wherein said pair of electrodes are spaced between 0.1 and 5 millimeters apart.

10. The implantable lead of claim 9, wherein said pair of electrodes are spaced between 0.5 and 1.5 millimeters apart.

11. An implantable lead for use with an implantable medical device, the implantable lead comprising:

at least two electrical conductors each having a proximal end and a distal end;

an insulation sheath covering said at least two electrical conductors;

an electrical connector affixed to said proximal end of each of said at least two electrical conductors and to said insulation sheath; and a bipolar active fixation electrode assembly affixed to said distal end of each of said at least two electrical conductors and to said insulation sheath, said bipolar active fixation electrode assembly having a distal end and a proximal end, said bipolar active fixation electrode assembly comprising a helix, said helix having a distal end and a proximal end, said helix comprising:

a cathode electrode; and an anode electrode, said cathode and anode electrodes being electrically spaced from one another by a distance of between 0.1 and 5.0 millimeters by an intermediate insulator.

12. The implantable lead of claim 11, wherein:

said cathode electrode comprises a center electrode at said distal end of said helix;

said anode electrode comprises an outer electrode proximal to said center electrode, said center electrode and said outer electrode being electrically separated by said intermediate insulator; and said bipolar active fixation electrode assembly further comprises an interconnect plug for providing an electrical interconnection between said at least two electrical conductors, said center electrode and said outer electrode.

13. The implantable lead of claim 11, wherein said insulation sheath is cylindrically shaped and wherein said bipolar active fixation electrode assembly is cylindrically shaped, whereby said bipolar active fixation electrode assembly is movable relative to said insulation sheath.

14. The implantable lead of claim 11, wherein said cathode and anode electrodes are electrically spaced from one another by a distance of between 0.5 and 1.5 millimeters by said intermediate insulator.

15. An implantable lead for use with an implantable medical device, the implantable lead comprising:

at least two electrical conductors encased in an insulation sheath, said electrical conductors and said insulation sheath extending from a proximal end to a distal end of said implantable lead;

a connector, affixed to said proximal end of said implantable lead, comprising at least two terminals electrically connected to respective ones of said at least two electrical conductors;

a cylindrical sheath attached to said distal end of said implantable lead;

a sleeve electrode affixed to said cylindrical sheath and adapted to make electrical contact with cardiac tissue;

an active fixation electrode assembly comprising a single means for penetrating the myocardium of a heart, said penetrating means having a distal end and a proximal end, said penetrating means comprising a tip electrode formed at said distal end thereof; an outer electrode coaxial with said tip electrode; and an intermediate insulator separating said outer electrode and said tip electrode, said active fixation electrode assembly positioned at said distal end of said implantable lead and electrically insulated from said sleeve electrode; and means for electrically interconnecting said tip electrode of said active fixation electrode assembly and said sleeve electrode to respective ones of said at least two electrical conductors of said implantable lead.

16. The implantable lead of claim 15, wherein said active fixation electrode assembly is cylindrically shaped, whereby said active fixation electrode assembly is movable with respect to said cylindrical sheath.

17. The implantable lead of claim 15, wherein means for penetrating the myocardium of a heart is formed into a helical coil.

18. The implantable lead of claim 17, wherein said at least two conductors comprises a third conductor electrically connected to said outer electrode; and wherein said means for interconnecting comprises means for providing an electrical interconnection between said third conductor and said outer electrode.

19. The implantable lead of claim 18, wherein:

said connector further comprises a third terminal electrically coupled to said third conductor;

whereby said outer electrode is electrically connected to said third terminal at said proximal end of said lead body.

20. The implantable lead of claim 15, wherein:

said outer electrode and said sleeve electrode are electrically connected together.

21. An electrode assembly comprising an active fixation helix having a pair of electrodes electrically separated by an intermediate insulator.

22. The electrode assembly of claim 21, wherein said pair of electrodes comprises:

a center electrode; and an outer electrode, said center electrode and said outer electrode being electrically separated by said intermediate insulator.

23. The electrode assembly of claim 21, wherein said pair of electrodes are spaced between 0.1 and 5 millimeters apart.

24. The electrode assembly of claim 21, wherein said pair of electrodes are spaced between 0.5 and 1.5 millimeters apart.

25. The electrode assembly of claim 21, further comprising a sleeve electrode.

26. The electrode assembly of claim 25, wherein said sleeve electrode and one of said pair of electrodes are electrically connected together.

27. An electrode assembly comprising an active fixation helix having a pair of electrodes, each one of said pair of electrodes being disposed along a portion of the coil of the helix, the pair of electrodes being electrically separated by an intermediate insulator.

* * * * *